United States Patent [19]
Hattler

[11] Patent Number: 5,865,789
[45] Date of Patent: Feb. 2, 1999

[54] PERCUTANEOUS OXYGENATOR FOR INDUCING A RETROGRADE PERFUSION OF OXYGENATED BLOOD

[76] Inventor: Brack G. Hattler, 5226 Westminster Pl., Pittsburgh, Pa. 15232

[21] Appl. No.: 899,018

[22] Filed: Jul. 23, 1997

[51] Int. Cl.⁶ .......................... A61M 37/00; A61M 29/00
[52] U.S. Cl. .............................................. 604/26; 604/101
[58] Field of Search .................. 604/23, 93, 96, 604/101, 26; 623/3

[56] References Cited

U.S. PATENT DOCUMENTS

| | | | |
|---|---|---|---|
| 4,686,973 | 8/1987 | Frisch | 623/23 |
| 4,883,459 | 11/1989 | Calderon | 604/28 |
| 4,911,689 | 3/1990 | Hattler | 604/26 |
| 4,986,809 | 1/1991 | Hattler | 604/26 |
| 5,122,113 | 6/1992 | Hattler | 604/26 |
| 5,186,713 | 2/1993 | Raible | 604/4 |
| 5,207,640 | 5/1993 | Hattler et al. | 604/28 |
| 5,219,326 | 6/1993 | Hattler | 604/26 |
| 5,376,069 | 12/1994 | Hattler | 604/26 |
| 5,451,207 | 9/1995 | Yock | 604/53 |
| 5,458,574 | 10/1995 | Machold et al. | 604/101 |
| 5,466,216 | 11/1995 | Brown et al. | 604/33 |
| 5,501,663 | 3/1996 | Hattler et al. | 604/26 |
| 5,558,644 | 9/1996 | Boyd et al. | 604/96 |
| 5,584,803 | 12/1996 | Stevens et al. | 604/4 |

*Primary Examiner*—Wynn Wood Coggins
*Assistant Examiner*—Sharon Finkel
*Attorney, Agent, or Firm*—Dorr, Carson, Sloan & Birney, P.C.

[57] ABSTRACT

A percutaneous oxygenator is used to induce a retrograde perfusion of oxygenated blood in a vein to a compromised organ (e.g., to the brain following a stroke, or to the heart following a heart attack). The oxygenator has an occluding balloon and an oxygenation balloon located upstream from the occluding balloon. A plurality of hollow gas-permeable fibers surround the oxygenation balloon. The oxygenator is inserted into a vein downstream from the compromised organ. An external supply of air/oxygen is connected to create a flow through the fibers and thereby oxygenate blood in the surrounding vein. A retrograde flow of oxygenated blood is induced in the vein to the compromised organ by first inflating the occluding balloon to occlude the vein and then inflating the oxygenation balloon. Both balloons are then deflated to permit the normal antegrade flow of blood through the vein. This process of inflation and deflation is periodically repeated at a rate of about 30 to 60 cycles per minute. The percutaneous oxygenator may be equipped with multiple occluding balloons for blocking several branches of the venous system leading from the compromised organ.

18 Claims, 5 Drawing Sheets

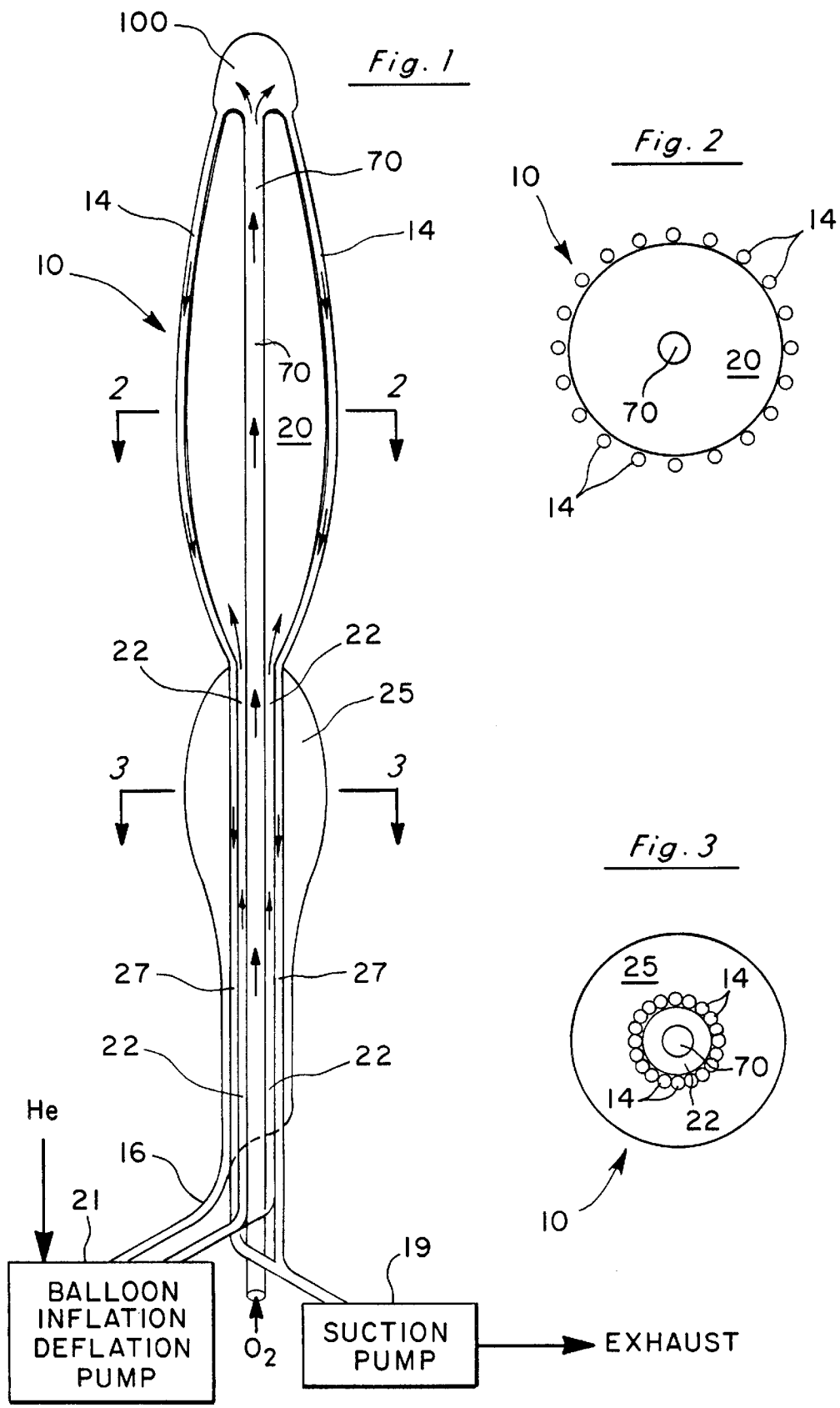

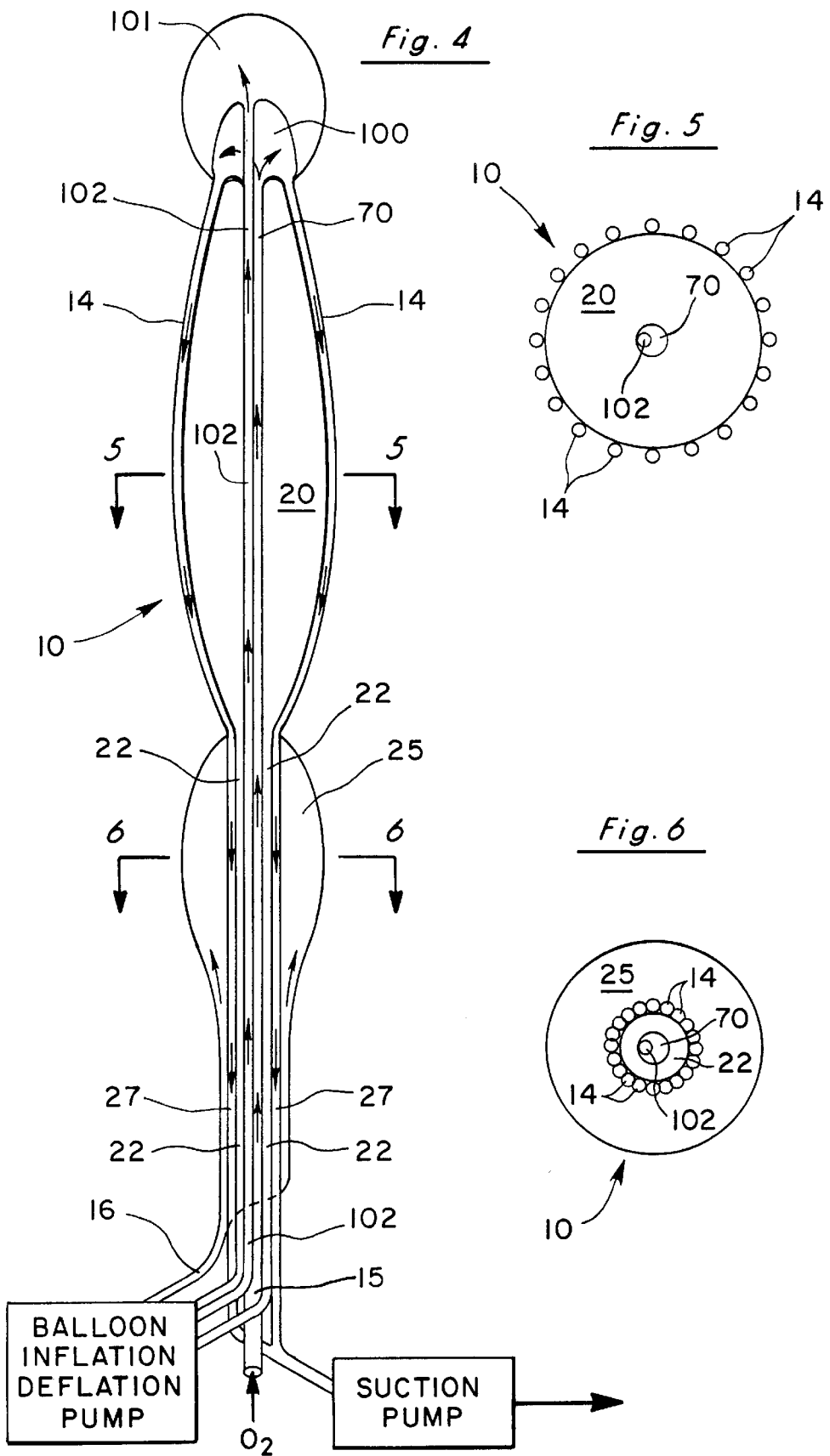

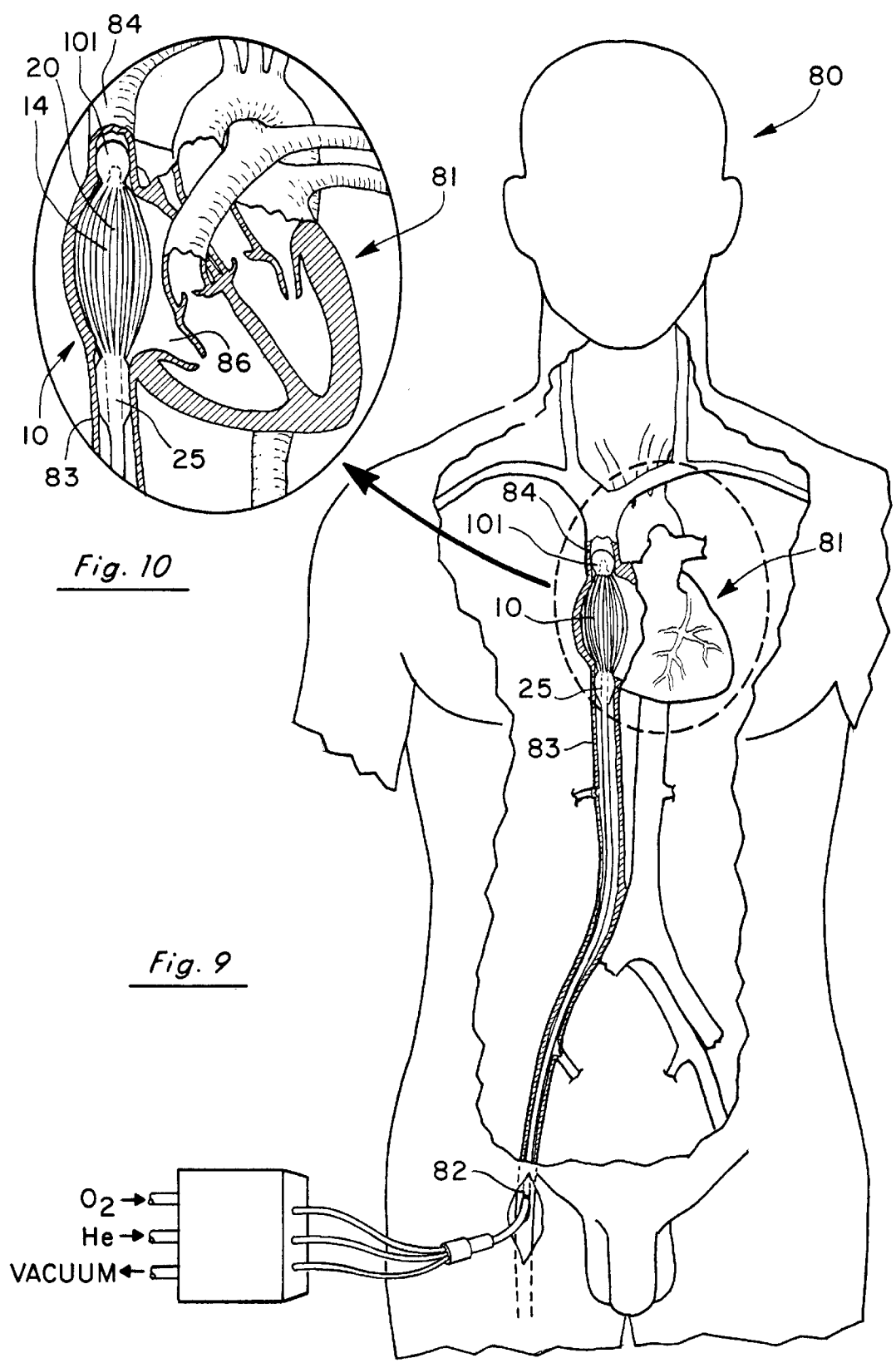

PERCUTANEOUS OXYGENATOR FOR INDUCING A RETROGRADE PERFUSION OF OXYGENATED BLOOD

BACKGROUND OF THE INVENTION

1. Field of the Invention

The present invention relates generally to the field of percutaneous oxygenators. More specifically, the present invention discloses a system for inducing a retrograde flow of oxygenated blood to a compromised organ within the body.

2. Statement of the Problem

It has been recognized for centuries that oxygenated blood is transported from the heart through arteries of progressively diminishing size ending in arterial capillaries that provide oxygen to the tissues that make up various organs. Blood that has been depleted of oxygen in these organs then gathers in venous capillaries and is carried back to the heart through a progressively enlarging venous system, ending in the superior and inferior vena cava, which deliver venous blood (which is low in oxygen content and high in carbon dioxide content) to the right atrium of the heart. At the capillary level, the arterial and venous capillaries interconnect so that blood flow which is normally antegrade from the arterial to the venous side, can potentially flow retrograde from the venous to the arterial side. The ability to nourish organs by providing oxygenated blood in a retrograde fashion has been used to provide retrograde perfusion to both the heart and the brain during complex surgical procedures on the heart and the great vessels (i.e., ascending aorta). However, this requires the use of complicated externally-situated pumps and oxygenators.

A variety of percutaneous oxygenators and systems for inducing retrograde fluid flow for other purposes have been used in the past, including the following:

| Inventor | U.S. Pat. No. | Issue Date |
| --- | --- | --- |
| Stevens et al. | 5,584,803 | Dec. 17, 1996 |
| Boyd et al. | 5,558,644 | Sep. 24, 1996 |
| Hattler et al. | 5,501,663 | Mar. 26, 1996 |
| Brown et al. | 5,466,216 | Nov. 14, 1995 |
| Machold et al. | 5,458,574 | Oct. 17, 1995 |
| Yock | 5,451,207 | Sep. 19, 1995 |
| Hattler | 5,376,069 | Dec. 27, 1994 |
| Hattler | 5,219,326 | June 15, 1993 |
| Hattler | 5,207,640 | May 4, 1993 |
| Hattler | 5,122,113 | June 16, 1992 |
| Hattler | 4,911,689 | Mar. 27, 1990 |
| Hattler | 4,986,809 | Jan. 22, 1991 |
| Calderon | 4,883,459 | Nov. 28, 1989 |

U.S. Pat. Nos. 5,584,803 (Stevens et al.), 5,458,574 (Machold et al.), and 5,558,644 (Boyd et al.) are a family of patents relating to the same general invention. The heart muscle is paralyzed by the antegrade or retrograde delivery of a cardioplegic fluid through the patient's coronary arteries or coronary sinus. An external cardiopulmonary bypass system 18 is used to deliver oxygenated blood to the arterial system during the procedure.

U.S. Pat. No. 5,466,216 (Brown et al.) discloses another example of an antegrade/retrograde cardioplegia system.

U.S. Pat. No. 5,451,207 (Yock) discloses a method for removing coronary plaque that includes a combination of bypass of the heart and retrograde perfusion of the heart.

U.S. Pat. No. 4,883,459 (Calderon) discloses a system for retrograde perfusion of tumors in chemotherapy.

The Hattler '689 and '809 patents disclose a percutaneous oxygenator having a Y-shaped tubular connector and a plurality of hollow, gas-permeable fibers. One end of each fiber is located in the first upper arm of the connector. The other end of each fiber is located in the other upper arm of the connector, with each fiber forming a loop extending out of the lower opening of the connector. To guide insertion, a support member extends downward from the connector with an aperture at its distal end. Each of the fiber loops passes through this aperture.

The Hattler '113 and '326 patents disclose an inflatable percutaneous oxygenator having an inflatable balloon suitable for insertion into a blood vessel. Oxygen is circulated through a plurality of hollow gas-permeable fibers adjacent to the balloon surface to permit diffusion of oxygen and carbon dioxide between the blood vessel and the fibers. A pump alternately expands and contracts the balloon. This causes movement of the fibers within the blood vessel to minimize streaming or channeling of the blood flow around the oxygenator, maximize turbulence in the blood stream, and therefore maximize diffusion of gases.

The Hattler '640 patent discloses a method for anesthetizing a patient using a structure with hollow gas-permeable fibers similar to that disclosed in the Hattler '113 patent.

The Hattler '069 patent discloses an inflatable percutaneous oxygenator with an internal support. Oxygen is circulated through a plurality of hollow gas-permeable fibers adjacent to the balloon surface to permit diffusion of oxygen and carbon dioxide between the blood vessel and the fibers. A pump alternately expands and contracts the balloon. In one embodiment, the balloon has a number of chambers separated by constrictions that restrict the flow of gases between the chambers. This results in a relative phase shift in the inflation and deflation of the balloon chambers to provide peristaltic motion of the balloon. Pulsatile flow can be used to increase the rate of cross-diffusion of gases between the fibers and the surrounding blood stream.

U.S. Pat. No. 5,501,663 (Hattler et al.) discloses an inflatable percutaneous oxygenator with transverse hollow fibers.

3. Solution to the Problem

None of the prior art references listed above show a percutaneous oxygenator that can be used to induce a retrograde flow of oxygenated blood to a compromised organ. Although the structure of the percutaneous oxygenator used in the present invention bears similarities to those disclosed in the previous Hattler patents, the present invention employs a percutaneous oxygenator having at least one occluding balloon to temporarily occlude the vein downstream from the compromised organ. In addition, the method used in the present invention is neither taught nor suggested by the prior art.

SUMMARY OF THE INVENTION

This invention provides a percutaneous oxygenator for inducing a retrograde perfusion of oxygenated blood in a vein to a compromised organ (e.g., to the brain following a stroke, or to the heart following a heart attack). The oxygenator has an occluding balloon and an oxygenation balloon located upstream from the occluding balloon. A plurality of hollow gas-permeable fibers surround the oxygenation balloon. The oxygenator is inserted into a vein downstream from the compromised organ. An external supply of air/oxygen is connected to create a flow through the fibers and thereby oxygenate blood in the surrounding vein. A retrograde flow of oxygenated blood is induced in the vein to the compromised organ by first inflating the occluding balloon to occlude the vein and then inflating the oxygenation balloon. Both balloons are then deflated to permit the normal antegrade flow of blood through the vein. This process of inflation and deflation is periodically repeated at a rate of about 30 to 60 cycles per minute or greater. The percutaneous oxygenator may be equipped with multiple occluding balloons for blocking several branches of the venous system leading from the compromised organ.

A primary object of the present invention is to provide an improved method and apparatus for supplying oxygenated blood to a compromised organ, particularly in cases where the normal arterial blood supply to the organ has been impaired.

Another object of the present invention is to provide a system for supplying oxygenated blood to a compromised organ that can be quickly implemented in emergency situations.

Yet another object of the present invention is to provide a system for supplying oxygenated blood to a compromised organ that is minimally invasive to the patient.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a side cross-sectional view of the percutaneous oxygenator 10 with a proximal occluding balloon 25.

FIG. 2 is a cross-sectional view of the percutaneous oxygenator 10 corresponding to FIG. 1, showing the oxygenation balloon 20.

FIG. 3 is another cross-sectional view of the percutaneous oxygenator 10 corresponding to FIG. 1, showing the proximal occluding balloon 25.

FIG. 4 is a side cross-sectional view of an alternative embodiment of the percutaneous oxygenator 10 with a proximal occluding balloon 25 and a distal occluding balloon 101.

FIG. 5 is a cross-sectional view of the percutaneous oxygenator 10 corresponding to FIG. 4, showing the oxygenation balloon 20.

FIG. 6 is another cross-sectional view of the percutaneous oxygenator 10 corresponding to FIG. 4, showing the proximal occluding balloon 25.

FIG. 9 is a front sectional view of a patient receiving selective retrograde perfusion of oxygenated blood in the right atrium following occlusion of a coronary artery (i.e., following a heart attack). Blood is forced retrograde in the coronary veins to oxygenate the heart muscle. The oxygenator and sections of the veins are shown in cross-section.

FIG. 10 is a front sectional view corresponding to FIG. 9 showing the oxygenator in position within the superior vena cava, right atrium of the heart, and inferior vena cava.

DETAILED DESCRIPTION OF THE INVENTION

Figures 7, 8:
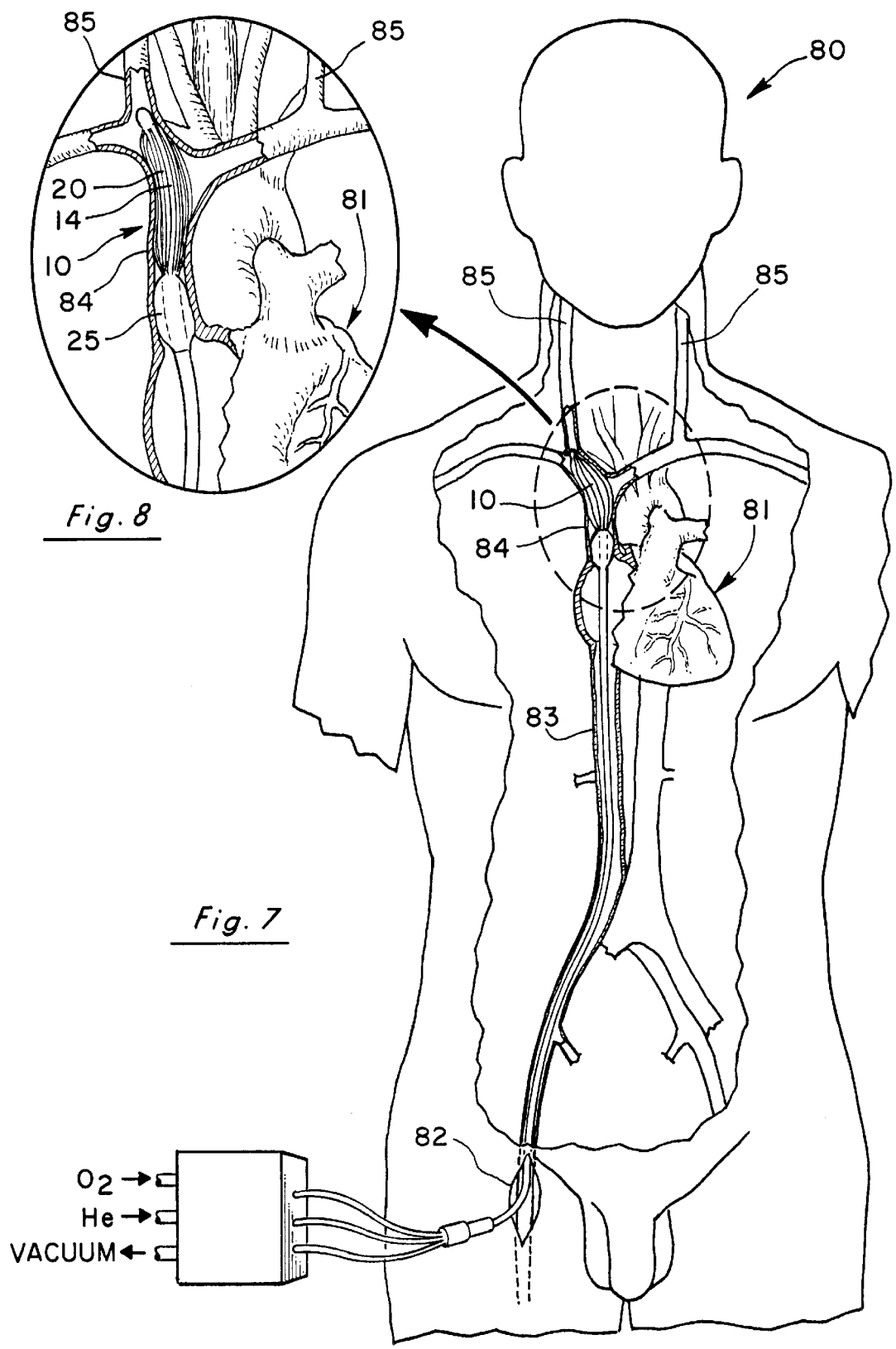
FIG. 7 is a front sectional view of a patient receiving selective retrograde perfusion of oxygenated blood in the superior vena cava following occlusion of a carotid artery (i.e., following a stroke). Blood is forced retrograde in the jugular veins to oxygenate the brain. The oxygenator and sections of the superior vena cava and jugular veins are shown in cross-section.
FIG. 8 is a front sectional view corresponding to FIG. 7 showing the oxygenator in position within the superior vena cava.

The present invention provides a simple device that is rapidly insertable into the venous system, is minimally invasive, and can provide retrograde perfusion of oxygenated blood to compromised organs as a result of either chronically or acutely obstructed arteries. Organs that could be accessed with the device include: the brain from occlusion of a vertebral, carotid or intracerebral artery; the upper extremities from an occlusion of the subclavian artery or from spasm of a vessel leading to that extremity; the heart from occlusion of a coronary artery; the liver from occlusion of the hepatic artery; the intestines from occlusion of the celiac, superior mesenteric, or inferior mesenteric arteries; the kidney from occlusion of a renal artery; the lower extremities from occlusion of an iliac, femoral, profundus femoral, or popliteal artery.

The basic principle for retrograde perfusion with oxygenated blood in the venous system under intermittent positive pressure would be the same for all organs. The target organ is isolated with an occluding balloon or balloons, proximal and distal to the target organ, while oxygenated blood is pumped retrograde to the compromised organ or target area.

Structure of Percutaneous Oxygenator

FIGS. 1 through 6 illustrate two embodiments of the percutaneous oxygenator 10 used in the present invention. FIG. 1 is a side cross-sectional view of a first embodiment of the oxygenator 10. The major components are an inflatable oxygenation balloon 20, a large number of hollow gas-permeable fibers 14 that surround at least a portion of the oxygenation balloon 20, and a smaller, inflatable occluding balloon 25 at the proximal end of the device 10. FIGS. 2 and 3 are cross-sectional views corresponding to FIG. 1 showing the oxygenation balloon 20 and proximal occluding balloon 25, respectively. In both embodiments, the oxygenation balloon 20 has an elongated shape with gas-permeable fibers 14 surrounding its exterior surface to form a substantially continuous sheath about the oxygenation balloon 20.

The gas-permeable walls of the fibers 14 provide a large total surface area for diffusion of oxygen into the bloodstream and diffusion of carbon dioxide out of the bloodstream. Any of a variety of flexible hollow gas-permeable fibers currently available on the market, such as Mitsubishi KPF190M polypropylene fibers, are suitable for this purpose. The polypropylene fibers should be coated with a thin (e.g., 1 micron or less) gas permeable membrane, such as silicone rubber, and bonded with a non-thrombogenic component. Alternatively, multi-layered composite hollow fiber membranes can be used for this purpose, such as Mitsubishi MHF200L fibers. These fibers have a composite structure with an outer layer of microporous polyethylene, an intermediate layer of polyurethane that acts as a true membrane, and an inner layer of microporous polyethylene.

The oxygenator includes separate lumens as shown in cross-section in FIGS. 1 through 6. An external pump 21 is connected to the lumen 16 used to inflate and deflate the occluding balloon 25, and to the lumen 22 used to inflate and deflate the oxygenation balloon 20. Any gas or fluid can be pumped into and released from the occluding balloon 25 and oxygenation balloon 20 for this purpose. Helium offers the advantages of having very low viscosity and density for ease of pumping. Carbon dioxide as an inflation gas offers safety features and is quickly dissolved in the bloodstream in the event of balloon leakage.

After the oxygenator 10 has been implanted as described below, a supply or oxygen or air is connected to the lumen extending axially along the hollow, central support 70. This hollow support 70 also helps to guide insertion of the percutaneous oxygenator 10 into the vein. Oxygen flows through the lumen 70, enters the hollow tip member 100 at the distal end of the oxygenator 10, and returns through the interior passageways of the hollow fibers 14. Oxygen diffuses outwardly through the gas-permeable walls of the fibers 14 into the surrounding bloodstream. Carbon dioxide also diffuses inwardly from the bloodstream through these gas-permeable walls into the interior of the fibers 14. Carbon dioxide and any remaining oxygen in the fibers are vented to the atmosphere through lumen 27. Negative pressurization can be applied by means of a suction pump 19 connected to lumen 27 to enhance gas flow through the fibers 14, and to reduce any risk of gas bubbles escaping from the fibers 14 into the bloodstream. For example, in one embodiment, oxygen is supplied into the fibers 14 at a flow rate of approximately 1 to 3 liters per minute and a nominal pressure of approximately 6 to 15 mm Hg. A suction pressure of approximately −150 to −250 mm Hg is applied by the suction pump 19.

FIG. 4 is a side cross-sectional view of an alternative embodiment of a percutaneous oxygenator 10 having a second occluding balloon 101 at its distal end. FIGS. 5 and 6 are cross-sectional views corresponding to FIG. 4 taken through the oxygenation balloon 20 and proximal occluding balloon 25, respectively. This embodiment includes an additional lumen 102 that enables the inflation/deflation pump 21 to independently inflate and deflate the second occluding balloon 101.

Method of Operation

Two specific examples of methods for using the present invention are illustrated in FIGS. 7 through 10. In both cases, the oxygenator 10 is initially inserted in the venous system through a single small incision. For example, the oxygenator 10 can be inserted through a small incision in the patient's femoral vein 82 and then advanced upward along the inferior vena cava 83 as depicted in FIGS. 7 and 9. The distal tip of the oxygenator 10 is inserted first so that the oxygenation balloon 20 is upstream from the occluding balloon 25. Both balloons 20, 25 remain deflated during this insertion process. When the oxygenator 10 is in position, an oxygen supply is connected to the central lumen 70 leading to the gas-permeable fibers 14. The suction pump 19 is connected to the lumen 27 drawing carbon dioxide and any remaining oxygen from the proximal ends of the fibers 14. The balloon inflation/deflation pump 21 is connected to lumens 16, 22 to inflate and deflate the occluding balloon 25 and oxygenation balloon 20.

Following implantation, the oxygenator 10 can be used to induce a retrograde flow of oxygenated blood in the vein to the compromised organ. First, the vein is occluded downstream from the compromised organ by inflating the occluding balloon 25. Next, the oxygenation balloon 20 is inflated to induce a retrograde flow of blood in the vein to the compromised organ. Both balloons 20, 25 are then deflated to allow normal antegrade flow of blood from the compromised organ through the vein. This sequence of steps is continuously repeated to maintain a supply of oxygenated blood to the compromised organ. A frequency of approximately 30 to 60 cycles per minute has been demonstrated to provide satisfactory results.

In a patient with an acute stroke from an obstructed carotid artery, the oxygenator 10 would be inserted so as to lie in the superior vena cava 84, or ipsilateral internal jugular vein 85. FIG. 7 is a front sectional view of a patient 80 receiving selective retrograde perfusion of oxygenated blood in the superior vena cava 84 following occlusion of a carotid artery (i.e., following a stroke). FIG. 8 is a front sectional view corresponding to FIG. 7 showing the oxygenator 10 in position within the superior vena cava 84. During the inflation cycle, the proximal occluding balloon 25 occludes the vein of residence when it is fully inflated. The larger elongated oxygenation balloon 20 situated just distal to the occluding balloon 25 is inflated in a delayed fashion after the occluding balloon 25 is inflated, thus propagating a pulsatile wave in the retrograde direction through the jugular veins 85 to supply oxygenated blood to the brain. During the deflation cycle, both balloons 20, 25 would empty, allowing venous blood to drain from the brain. The end result is that highly oxygenated blood would be supplied to the brain, not through the normal arterial pathway, but retrograde through the venous system. Such a configuration of the oxygenation balloon 20 and fibers 14 would also suffice for supplying blood to the upper extremities (vein of choice for implant, the subclavian vein) or the lower extremities (vein of choice for implant, the femoral vein).

FIG. 9 is a front sectional view of a patient 80 receiving selective retrograde perfusion of oxygenated blood in the right atrium 86 following occlusion of a coronary artery (i.e., following a heart attack). Blood is forced retrograde in the coronary veins to oxygenate the heart muscle using the alternative embodiment of the oxygenator 10 with two occluding balloons 101, 25 as shown in FIGS. 4 through 6. FIG. 10 is a front sectional view corresponding to FIG. 9 showing the oxygenator 10 in position within the superior vena cava 84, right atrium 86 of the heart 81, and inferior vena cava 83. With these occluding balloons 101, 25 thus situated in the superior and inferior vena cavas 84 and 83, the oxygenation balloon 20 resides in their middle and is positioned in the right atrium 86.

In normal antegrade blood circulation, the cardiac veins drain the capillary networks of the myocardium and drain into the right atrium 86 by way of the coronary sinus, or drain directly into the right atrium 86. In contrast, the present invention reverses this flow by forcing oxygenated blood retrograde from the right atrium into the coronary sinus during balloon inflation and thereby nourishes the heart.

Figures 11, 12:
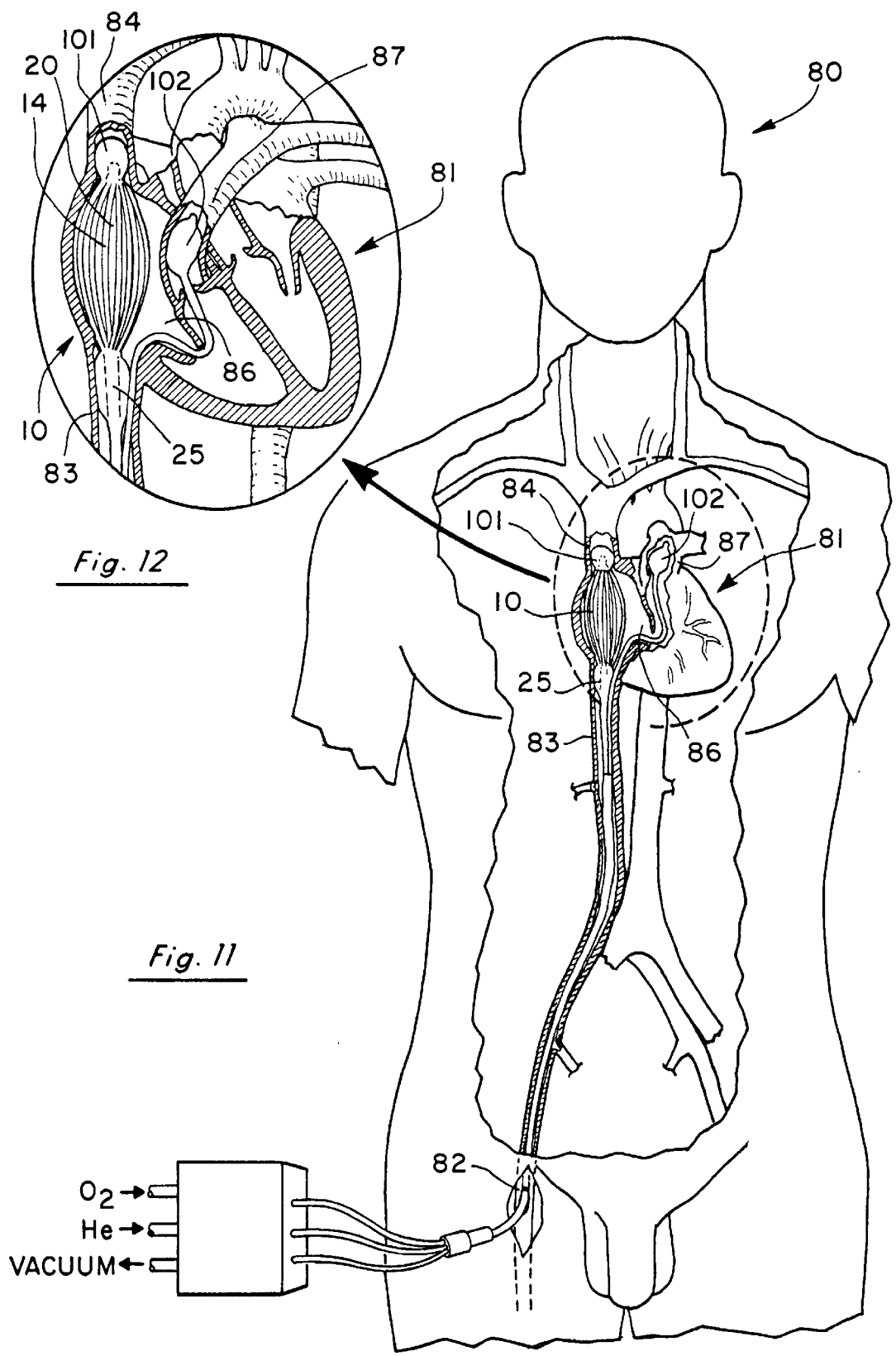
FIG. 11 is a front sectional view of a patient receiving selective retrograde perfusion of oxygenated blood in the right atrium using an alternative embodiment of the present invention following a heart attack. The oxygenator and sections of the veins are shown in cross-section.
FIG. 12 is a front sectional view corresponding to FIG. 11 showing the oxygenator in position within the superior vena cava, right atrium of the heart, and inferior vena cava. The third balloon 102 connected by a separate catheter occludes the pulmonary artery 87.

FIGS. 11 and 12 depict yet another embodiment of the present invention having a third inflatable balloon 102 that is similar to occluding balloons 101 and 25, but is used to occlude the pulmonary artery 87. This provides a more complete isolation of the right atrium 86 and right ventricle. The oxygenation balloon 20 thereby becomes more effective in directing a flow of oxygenated blood from the right atrium 86 into the coronary sinus since blood is no longer capable of exiting via the pulmonary artery 87.

In the embodiment shown in FIGS. 11 and 12, the third balloon 102 is inflated and deflated through a separate catheter that branches off the main catheter leading to the other balloons 101, 25. The third balloon is inserted through a small incision in the femoral vein 82 and then advanced upward along the inferior vena cava 83. It is then advance through the right atrium 86 and the right ventricle of the heart into the pulmonary artery 87. After implantation, the balloon inflation/deflation pump 21 is connected to the catheter leading to the third balloon 102 so that it will be periodically inflated and deflated in the same manner as the other balloons 101, 25.

For the kidney, liver, or intestines, two occluding balloons 25, 101 in the inferior vena cava would also be necessary, positioned proximal and distal to the organ of concern. The oxygenation balloon 20 is located between the two occluding balloons 25, 101 and during inflation its transmitted pulse would be isolated from the rest of the venous system, thus forcing oxygenated blood retrograde up the compromised organ to supply oxygen. As in all instances during the deflation cycle, blood is allowed to drain from the compromised organ, thus preventing engorgement and edema of the organ.

The above disclosure sets forth a number of embodiments of the present invention. Other arrangements or embodiments, not precisely set forth, could be practiced under the teachings of the present invention and as set forth in the following claims.

I claim:

1. A method for inducing retrograde perfusion of oxygenated blood in a vein to a compromised organ, said method comprising:
   inserting a percutaneous oxygenator into the vein, said percutaneous oxygenator having:
   (a) an occluding balloon;
   (b) an oxygenation balloon upstream from said occluding balloon; and
   (c) a plurality of hollow gas-permeable fibers surrounding at least a portion of said oxygenation balloon;
   providing a flow of air/oxygen through said fibers to oxygenate blood in the surrounding vein; and
   periodically repeating the steps of:
   (a) inflating said occluding balloon to occlude the vein downstream from the compromised organ;
   (b) inflating said oxygenation balloon to induce a retrograde flow of blood to the compromised organ; and
   (c) deflating said occluding balloon and said oxygenation balloon to allow normal antegrade flow of blood through the vein.

2. The method of claim 1 wherein said percutaneous oxygenator is inserted through an incision in the patient's femoral vein.

3. The method of claim 1 wherein said percutaneous oxygenator is inserted into the patient's superior vena cava to induce a retrograde flow through the jugular veins to the brain.

4. The method of claim 1 wherein said occluding balloon and said oxygenation balloon are inflated and deflated at a frequency of approximately 30 to 60 cycles per minute.

5. The method of claim 1 wherein said percutaneous oxygenator further comprises an elongated support for guiding insertion of said percutaneous oxygenator into the vein.

6. The method of claim 1 wherein said oxygenation balloon further comprises an elongated balloon sheathed with said gas-permeable fibers.

7. A percutaneous oxygenator for inducing retrograde perfusion of oxygenated blood in a vein to a compromised organ comprising:
   an occluding balloon;
   an oxygenation balloon upstream from said occluding balloon;
   a plurality of hollow gas-permeable fibers surrounding at least a portion of said oxygenation balloon;
   means for supplying a flow of air/oxygen through said fibers to oxygenate blood in the surrounding vein; and
   means for periodically inflating said occluding balloon to occlude said vein, inflating said oxygenation balloon to induce a retrograde flow of blood in the vein to the compromised organ, and then deflating said occluding balloon and said oxygenation balloon to allow normal antegrade flow of blood through said vein.

8. The percutaneous oxygenator of claim 7 wherein said occluding balloon and said oxygenation balloon are inflated and deflated at a frequency of approximately 30 to 60 cycles per minute.

9. The percutaneous oxygenator of claim 7 wherein said percutaneous oxygenator further comprises an elongated support for guiding insertion of said percutaneous oxygenator into the vein.

10. The percutaneous oxygenator of claim 7 wherein said oxygenation balloon further comprises an elongated balloon sheathed with said gas-permeable fibers.

11. The percutaneous oxygenator of claim 7 further comprising a second occluding balloon at the distal end of said oxygenation balloon.

12. A method for inducing retrograde perfusion of oxygenated blood to the heart, said method comprising:
    inserting a percutaneous oxygenator into the heart, said percutaneous oxygenator having:
    (a) a first occluding balloon positioned in the superior vena cava;
    (b) a second occluding balloon positioned in the inferior vena cava;
    (c) an oxygenation balloon between said first and second occluding balloons positioned in the right atrium of the heart; and
    (d) a plurality of hollow gas-permeable fibers surrounding at least a portion of said oxygenation balloon;
    providing a flow of air/oxygen through said fibers to oxygenate blood in the right atrium of the heart; and
    periodically repeating the steps of:
    (a) inflating said occluding balloons to occlude the superior vena cava and inferior vena cava;
    (b) inflating said oxygenation balloon to induce a retrograde flow of blood from the right atrium of the heart to the coronary sinus; and
    (c) deflating said occluding balloons and said oxygenation balloon to allow normal antegrade flow of blood through the superior vena cava and inferior vena cava into the right atrium of the heart.

13. The method of claim 12 wherein said percutaneous oxygenator is inserted through an incision in the patient's femoral vein and advanced along the inferior vena cava into the right atrium of the heart.

14. The method of claim 12 wherein said occluding balloons and said oxygenation balloon are inflated and deflated at a frequency of approximately 30 to 60 cycles per minute.

15. The method of claim 12 wherein said oxygenation balloon further comprises an elongated balloon sheathed with said gas-permeable fibers.

16. A method for inducing retrograde perfusion of oxygenated blood to the brain of a patient, said method comprising:

inserting a percutaneous oxygenator into the patient's superior vena cava, said percutaneous oxygenator having:
 (a) an occluding balloon;
 (b) an oxygenation balloon upstream from said occluding balloon; and
 (c) a plurality of hollow gas-permeable fibers surrounding at least a portion of said oxygenation balloon;

providing a flow of air/oxygen through said fibers to oxygenate blood in the superior vena cava; and periodically repeating the steps of:
 (a) inflating said occluding balloon to occlude the superior vena cava;
 (b) inflating said oxygenation balloon to induce a retrograde flow of blood through the jugular veins to the brain; and
 (c) deflating said occluding balloon and said oxygenation balloon to allow normal antegrade flow of blood through the jugular veins and superior vena cava.

17. The method of claim 16 wherein said oxygenator is inserted through an incision in the patient's femoral vein and advanced into the superior vena cava.

18. The method of claim 16 wherein said occluding balloon and said oxygenation balloon are inflated and deflated at a frequency of approximately 30 to 60 cycles per minute.

* * * * *